(12) United States Patent
Collinge et al.

(10) Patent No.: US 7,550,144 B2
(45) Date of Patent: Jun. 23, 2009

(54) PRION INHIBITION

(75) Inventors: John Collinge, London (GB); Simon Hawke, London (GB)

(73) Assignee: D-Gen Limited, London (GB)

( * ) Notice: Subject to any disclaimer, the term of this patent is extended or adjusted under 35 U.S.C. 154(b) by 169 days.

(21) Appl. No.: 10/535,938

(22) PCT Filed: Nov. 28, 2003

(86) PCT No.: PCT/GB03/05225
§ 371 (c)(1),
(2), (4) Date: Jun. 2, 2006

(87) PCT Pub. No.: WO2004/050120
PCT Pub. Date: Jun. 17, 2004

(65) Prior Publication Data
US 2006/0280745 A1    Dec. 14, 2006

(30) Foreign Application Priority Data
Nov. 29, 2002   (GB)  .................................  0227886.9

(51) Int. Cl.
*A61K 39/395*   (2006.01)
*A61K 39/04*    (2006.01)
*A61K 38/00*    (2006.01)

(52) U.S. Cl. .................. 424/184; 424/248.1; 424/139.1; 424/141.1; 530/388.15; 530/324

(58) Field of Classification Search ........................ None
See application file for complete search history.

(56) References Cited

U.S. PATENT DOCUMENTS

2003/0049249 A1   3/2003   Weissmann et al.

FOREIGN PATENT DOCUMENTS

| WO | WO-97/10505 | 3/1997 |
| WO | WO-98/37210 | 8/1998 |
| WO | WO-00/78344 | 12/2000 |
| WO | WO-02/087502 | 11/2002 |
| WO | WO-03/025181 | 3/2003 |
| WO | WO-03/080665 | 10/2003 |

OTHER PUBLICATIONS

Peretz et al (2001) Nature. 412:739-743.*
White et al (2003) Nature. 422: 80-83.*
Paul, Fundamental Immunology, 3rd Edition, 1993, pp. 292-295, under the heading "Fv Structure and Diversity in Three Dimensions".*
Rudikoff et al (Proc. Natl. Acad. Sci. USA, 79(6):1979-1983, Mar. 1982).*
MacCallum et al (J. Mol. Biol., 262, 732-744, 1996).*
Casset et al (Biochemical and Biophysical Research Communications, 307:198-205, 2003).*
Coleman P. M. (Research in Immunology, 145:33-36, 1994).*
Altschul et al., J. Mol. Biol., 215:403-410 (1990).
Anstee et al., Immunology, 74:197-205 (1991).
Avent et al., Biochem. J., 256:1043-1046 (1988).
Beringue et al., Brain, 126:2065-2073 (2003).
Brown, Neurology, 58:1720-1725 (2002).
Collins et al., Ann. Neurol., 52:503-506 (2002).
Dickinson et al., J. Comp. Pathol., 78:293-299 (1968).
Farquhar et al., Lancet, 353:117 (1999).
Jackson et al., Biochim. Biophys. Acta, 1431:1-13 (1999).
Sethi et al., Lancet, 360:229-230 (2002).
Sigurdsson et al., Neurosci. Lett., 336: 185-187 (2003).
Souan et al., Eur. J. Immunol., 31:2338-2346 (2001).
Wadsworth et al., Lancet, 358:171-180 (2001).
Westaway et al., Trends Biochem Sci., 27(6):301-307 (2002).
Will et al., Lancet, 347:921-925 (1996).
Bard et al., Nat. Med., 6(8):916-919 (2000).
Beringue et al., J. Virol., 74(12):5432-5440 (2000).
Brandner et al., Nature, 379:339-343 (1996).
Brown et al., Nat. Med., 5(11):1308-1312 (1999).
Bruce et al., Nature, 389(6650):498-501 (1997).
Bueler et al., Nature, 356:577-582 (1992).
Collinge et al., Nature, 383:685-690 (1996).
Devereux et al., Nucleic Acids Res., 12(1):387-395 (1984).
Enari et al., Proc. Natl. Acad. Sci. USA, 98(16):9295-9299 (2001).
Heppner et al., Science, 294:178-182 (2001).
Hill et al., Nature, 389:448-450 (1997).
Ingrosso et al., J. Virol., 69(1):506-508 (1995).
Jackson et al., Science, 283:1935-1937 (1999).
Klein et al., Nat. Med., 4(12):1429-1433 (1998).
Korth et al., Proc., Natl. Acad. Sci, USA, 98(17):9836-9841 (2001).
McKenzie et al., J. Virol., 68(11):7534-7536 (1994).
Montrasio et al., Science, 288:1257-1259 (2000).
Peretz et al., Nature, 412:739-743 (2001).
Prusiner, Proc. Natl. Acad. Sci. USA, 95:13363-13383 (1998).
Sigurdsson et al., Am. J. Pathol., 161(1):13-17 (2002).
Thompson et al., Nucleic Acids Res., 22(22):4673-4680 (1994).
White et al., Nature, 422:80-83 (2003).

* cited by examiner

*Primary Examiner*—Gary B. Nickol
*Assistant Examiner*—Michelle Horning
(74) *Attorney, Agent, or Firm*—McAndrews, Held & Malloy Ltd.

(57) ABSTRACT

The invention relates to the use of an agent such as an antibody capable of reacting with PrP in the prevention of prion replication in a subject, in the treatment or prevention of prion infection, in the treatment or prevention of neuropathology associated with prion infection or in the preparation of a medicament for the treatment or prevention of prion disease. Furthermore, the invention relates to methods of treatment of prion disease, methods of inhibiting prion replication and antibodies for use in such methods.

12 Claims, 6 Drawing Sheets

PRION INHIBITION

This application is a U.S. National Phase Application pursuant to 35 U.S.C. 371 of International Application No. PCT/GB2003/005225 which was filed Nov. 28, 2003, claiming benefit of priority of British Patent Application No. 0227886.9 filed Nov. 29, 2002. The entire disclosure of each of the foregoing applications is incorporated herein by reference.

Prion diseases such as Creutzfeldt-Jakob disease (CJD) are fatal, neuro-degenerative disorders for which therapy is ineffective. A proportion of the UK population has been exposed to a bovine spongiform encephalopathy (BSE)-like prion strain[1-3] and are at risk of developing variant CJD[4].

A hallmark of prion disease is the transformation of normal cellular prion protein (PrP$^c$) into an infectious disease-associated isoform[5], PrP$^{Sc}$.

Previous in vivo studies aimed at inhibiting prions or prion infection in whole organisms have not succeeded, in particular they have not succeeded in preventing the development of clinical prion disease.

Where attempts have been made to neutralise prions in vivo in the prior art, these have been in systems in which prion replication is not underway. For example, such prior art studies either amount to mixing of prion inoculum with neutralising agent before introduction into the organism, or merely introduce prion inoculum into a system already loaded with neutralisation agent such that the prion(s) never have the opportunity to establish or replicate in vivo.

In vivo studies of compounds known to show promising properties in in vitro experiments clearly illustrate in vitro behaviour of such compounds does not lead to any kind of performance in vivo. Examples of this may be found in the study of quinacrine which may have showed promise in vitro but this was not borne out by any clinical effect in vivo (eg. see PNAS 2001 vol 98 pp 9836-41 and Ann Neurol. 2002 vol 52 pp 503-6).

Furthermore, there is no previously known in vivo system which has demonstrated an effective arrest or inhibition of prion replication.

The present invention seeks to overcome problem(s) associated with the prior art.

SUMMARY OF THE INVENTION

It is surprisingly shown herein that prion replication can be effectively inhibited in vivo. In contrast to existing studies, the present invention enables the inhibition of established and replicating populations of prions in vivo in whole organisms.

It is a core feature of the present invention that the methods and uses are effective in inhibiting replication of prions which have already entered the replication phase. Although it is advantageous to apply to the present invention to prophylactic and immunisation applications, a key advantage of the present invention is that it enables the arrest/inhibition of established populations of prions ie. it is effective when applied to subjects after the time of exposure, inoculation or infection, for example when applied at least seven days (or later—see below) after the time of exposure, inoculation or infection. Prior art techniques do not produce this advantageous effect. It is also an advantageous feature of the present invention that in addition to delaying or postponing such as through increased incubation times, the present invention enables the prevention/inhibition of prion disease.

Accordingly the invention provides the use of an antibody capable of reacting with PrP in the prevention of prion replication in a subject.

In another aspect, the invention relates to the use of an antibody capable of reacting with PrP in the treatment or prevention of prion infection.

In another aspect, the invention relates to the use of an antibody capable of reacting with PrP in the treatment or prevention of neuropathology associated with prion infection.

In another aspect, the invention relates to the use of an antibody capable of reacting with PrP in the preparation of a medicament for the treatment or prevention of prion disease.

In another aspect, the invention relates to the use as described above wherein said medicament is a vaccine.

In another aspect, the invention relates to a method of treating prion infection in a subject comprising administering to said subject an effective amount of an antibody capable of reacting with PrP.

In another aspect, the invention relates to a method as described above wherein the antibody is administered after the subject has been exposed to prions.

In another aspect, the invention relates to a method as described above wherein the antibody is administered at least seven days after the subject has been exposed to prions.

In another aspect, the invention relates to a method as described above wherein the antibody is administered within 120 days after the subject has been exposed to prions.

In another aspect, the invention relates to a method as described above wherein antibody is administered after at least 4% of the total mean incubation time for said subject.

In another aspect, the invention relates to a method as described above wherein antibody is administered within 62% of the total mean incubation time for said subject.

In another aspect, the invention relates to a method of immunising a subject against prion infection comprising administering to said subject an effective amount of an antibody capable of reacting with PrP.

In another aspect, the invention relates to a use as described above or a method as described above wherein said antibody was raised against PrP 91-231.

In another aspect, the invention relates to a use or a method as described above wherein said antibody reacts with PrP$^{Sc}$.

In another aspect, the invention relates to a use or a method as described above wherein said antibody reacts with PrP$^c$ and with PrP$^{Sc}$.

In another aspect, the invention relates to a use or a method as described above wherein said antibody is an IgG.

In another aspect, the invention relates to a use or a method as described above wherein said antibody is ICSM18 or a fragment or fusion thereof.

In another aspect, the invention relates to a use or a method as described above wherein said antibody is ICSM35 or a fragment or fusion thereof.

In another aspect, the invention relates to a method of inhibiting prion replication comprising contacting said prion with ICSM 18 antibody.

In another aspect, the invention relates to a method of inhibiting prion replication comprising contacting said prion with ICSM 35 antibody.

In another aspect, the invention relates to an antibody or fragment thereof comprising CDR amino acid sequence encoded by at least one nucleotide sequence selected from the group consisting of SEQ ID NO 1, SEQ ID NO 2, SEQ ID NO 3, and SEQ ID NO 4, or a homologue thereof.

In another aspect, the invention relates to a use or a method as described above wherein the antibody is an antibody or fragment thereof comprising CDR amino acid sequence encoded by at least one nucleotide sequence selected from the group consisting of SEQ ID NO 1, SEQ ID NO 2, SEQ ID NO 3, and SEQ ID NO 4, or a homologue thereof.

In another aspect, the invention relates to a use or a method as described above wherein the subject is a mammal.

In another aspect, the invention relates to a use or a method as described above wherein the subject is a primate.

In another aspect, the invention relates to a use or a method as described above wherein the subject is a human.

DETAILED DESCRIPTION OF THE INVENTION

It is demonstrated herein that agents such as monoclonal antibodies used in accordance with the invention inhibit prion replication in vivo. Furthermore, agents such as monoclonal antibodies used in accordance with the invention delay the development of prion disease.

It is demonstrated herein using a murine scrapie model that agents such as anti-PrP mAbs have inhibitory effects on prion replication in vivo. It is further shown that peripheral $PrP^{Sc}$ levels and prion infectivity are dramatically reduced, even when the antibodies are first administered at the point of near maximal splenic $PrP^{Sc}$ accumulation.

Furthermore, every animal in which the treatment has been continued remains clinically healthy >200 days after equivalent untreated animals have succumbed to the disease. Thus the present invention provides immunotherapeutic strategies for prion diseases.

Thus in one embodiment the invention provides the use of agents such as antibodies in the prevention and/or treatment of prion disease.

Prevention and/or treatment is intended to embrace arrest, suspension, stopping, containment, freezing, inhibition of expansion, inhibition of replication, prevention of escalation or increase of prion load or similar effect in a subject. Preferably treatment/prevention of disease includes at least the delay, postponement or deferral of onset of clinical symptoms.

The subject is an organism, preferably a mammal, preferably a primate, preferably a human.

Agent

The agent according to the present invention is an entity which is capable of inhibiting the replication of prion(s) in vivo in a subject. The agent of the present invention may comprise one or more antibodies or antibody fragments capable of binding prion protein, mimetics thereof or small molecule(s) capable of binding prion protein or combinations thereof. Preferably the agent of the invention is an antibody or fragment thereof, preferably a monoclonal antibody or fragment thereof. Preferably the agent of the invention comprises an antibody or antibody fragment capable of binding prion protein.

Preferably the agent of the invention is an antibody or fragment thereof which was raised against PrP 91-231

Preferably the agent of the invention is an antibody or fragment thereof which reacts with $PrP^{Sc}$ Preferably the agent of the invention is an antibody or fragment thereof which reacts with $PrP^c$ and with $PrP^{Sc}$ Preferably the agent of the invention is an antibody or fragment thereof which is an IgG.

In another embodiment, the antibody is preferably raised against alpha PrP, preferably the antibody is raised against alpha PrP 91-231.

Preferably the antibody reacts with $PrP^{Sc}$.
Preferably the antibody reacts with $PrP^c$ and with $PrP^{Sc}$.
Preferably the antibody reacts with PrP epitope 146-159.
Preferably the antibody is IgG.

Preferably the antibody is of the IgG1 subclass.
Preferably the antibody comprises at least the CDRs of SEQ ID NO 3 and/or SEQ ID NO 4.
Preferably the antibody is ICSM18 or a fragment or fusion thereof.

In another embodiment, the antibody is preferably raised against beta PrP, preferably raised against beta PrP 91-231.
Preferably the antibody reacts with $PrP^{Sc}$.
Preferably the antibody reacts with $PrP^c$ and with $PrP^{Sc}$.
Preferably the antibody reacts with PrP epitope 91-110.
Preferably the antibody is IgG.
Preferably the antibody is of the IgG2b subclass.
Preferably the antibody comprises at least the CDRs of SEQ ID NO 1 and/or SEQ ID NO 2.
Preferably the antibody is ICSM35 or a fragment or fusion thereof.

Advantageously when the agent is an antibody, said antibody is a humanised antibody. Humanisation of antibodies is well known in the art and can be easily accomplished by the skilled worker. For example, ICSM18 and/or ICSM35 may each be advantageously humanised with reference to the sequences encoding the CDRs presented herein. In this regard, SEQ ID NO 1 corresponds to ICSM35VH;
SEQ ID NO: 2 corresponds to ICSM35VK;
SEQ ID NO: 3 corresponds to ICSM18VH;
SEQ ID NO: 4 corresponds to ICSM18lc.

Guidance regarding humanisation may be found for example in the literature as published by Greg Winter et al., and techniques for the manipulation and production of recombinant antibodies may be found in Harlow and Lane 'Antibodies-A Laboratory Manual', Cold Spring Harbour press.

In one embodiment, the antibodies (or fragments) may advantageously be humanised by manufacture of chimaeric antibodies. In another embodiment, the antibodies (or fragments) may advantageously be CDR-grafted.

In another embodiment, the antibodies (or fragments) may advantageously be fully humanised to the extent that the technology permits.

Pharmaceutical Compositions

The present invention also provides a pharmaceutical composition comprising a therapeutically effective amount of the agent(s) of the present invention and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

Where the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

If the agent is a protein, then said protein may be prepared in situ in the subject being treated. In this respect, nucleotide sequences encoding said protein may be delivered by use of non-viral techniques (e.g. by use of liposomes) and/or viral techniques (e.g. by use of retroviral vectors) such that the said protein is expressed from said nucleotide sequence.

In a preferred embodiment, the pharmaceutical of the present invention is administered topically.

Hence, preferably the pharmaceutical is in a form that is suitable for topical delivery.

Administration

The term "administered" includes delivery by viral or non-viral techniques. Viral delivery mechanisms include but are not limited to adenoviral vectors, adeno-associated viral (AAV) vectos, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof.

The components of the present invention may be administered alone but will generally be administered as a pharmaceutical composition—e.g. when the components are is in admixture with a suitable pharmaceutical excipient, diluent or carrier selected with regard to the intended route of administration and standard pharmaceutical practice.

For example, the components can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

In a preferred aspect, the pharmaceutical composition is delivered topically.

It is to be understood that not all of the components of the pharmaceutical need be administered by the same route. Likewise, if the composition comprises more than one active component, then those components may be administered by different routes.

If a component of the present invention is administered parenterally, then examples of such administration include one or more of: intravenously, intra-arterially, intraperitoneally, intrathecally, intraventricularly, intraurethrally, intrasternally, intracranially, intramuscularly or subcutaneously administering the component; and/or by using infusion techniques.

For parenteral administration, the component is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

As indicated, the component(s) of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

Alternatively, the component(s) of the present invention can be administered in the form of a suppository or pessary, or it may be applied topically in the form of a gel, hydrogel, lotion, solution, cream, ointment or dusting powder. The component(s) of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the component(s) of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Advantageously the agent of the present invention is administered in such a way as to contact tissue(s) in which prions may accumulate. This may conveniently be accomplished by direct injection of a suitable formulation into the subject.

Approximately 0.1% of agent administered into a subject can be passively transported into the spinal fluid. This proportion may vary depending upon the exact mode of administration and the exact nature of the agent. Advantageously, techniques may be used in order to increase this proportion. Advantageously, direct application of the agent into the spinal fluid may be performed.

Clearly, it is advantageous for the agent to contact neural tissues in which prions are known to accumulate. For example, it is advantageous for the agent to be administered in such a way as to contact brain tissues. Crossing the Blood-Brain Barrier (BBB) is a problem known in the art and can be overcome by a person skilled in the art.

For example, the agent may be directly administered into the brain. This could be accomplished by direct infusion using a Omayer reservoir extending into the lateral ventricle in a manner similar to that used in the treatment of metastatic cancers such as testicular cancer.

In another example, the agent may be linked preferably covalently linked to a carrier peptide such as a ligand for the transferrin receptor such as an anti-transferrin receptor mAb or transferrin or a part thereof. In a preferred embodiment this linkage is achieved by fusion of the agent such as an antibody to the carrier such as transferrin. This may be advantageously accomplished by production and expression of a recombinant gene fusion encoding transferrin and the antibody or fragment of interest. In this manner, the agent may be administered to the subject via any suitable route and the subject's own transport mechanism(s) will allow the agent to cross the blood-brain barrier by action of the transferrin receptor.

In another example, the agent may be administered into the brain by use of non-virulent neurotropic viruses. One or more of these viruses are inoculated or infected into the subject. The blood brain barrier is then able to permit passive transfer of agent such as antibody into the brain. These regimes may be simply based on known systems such as those used in clearing alpha-virus and/or influenza-virus from the brain using antibodies. Agent(s) according to the present invention such as anti-PrP antibodies as described herein are simply substituted for the antiviral antibodies used in the existing techniques.

Timing of Administration

It is an advantage of the invention that the agent may be administered after exposure to prions.

Preferably the agent is administered as soon as is practical after exposure to prions.

Preferably the agent is administered before the onset of clinical symptoms.

Preferably the agent is administered before neuroinvasion (ie. before prions have populated the brain).

Preferably the agent is administered before peripheral neuroinvasion (ie. before prions have populated the spinal cord and/or the peripheral nerves.)

Preferably the agent is administered within 120 days of exposure, preferably within 117 days of exposure, preferably within 100 days of exposure, preferably within 80 days of exposure, preferably within 60 days of exposure, preferably within 40 days of exposure, preferably within 30 days of exposure, preferably within 20 days of exposure, preferably within 7 days of exposure.

More preferably the timing of administration is expressed in terms of a percentage of the total incubation period (mean incubation period). This enables different species' incubation times to be taken into account and appropriate adjustments made to the timing of administration. Advantageously the mouse mean total incubation time of 195 days as a calibration with reference to the Examples.

Preferably the agent is administered within 62% of the total incubation time, preferably within 60% of the total incubation time, preferably within 52% of the total incubation time, preferably within 41% of the total incubation time, preferably within 31% of the total incubation time, preferably within 21% of the total incubation time, preferably within 16% of the total incubation time, preferably within 11% of the total incubation time, preferably within 4% of the total incubation time.

If the exact time of the exposure to prions is not known then it will be apparent that an estimated time of exposure to prions should be used in the estimation of the total incubation times and therefore the timing of the administration.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Depending upon the need, the agent may be administered at a dose of from 0.01 to 30 mg/kg body weight, such as from 0.1 to 10 mg/kg, more preferably from 0.1 to 1 mg/kg body weight. Preferably dosage may be estimated according to the dosages used in the accompanying Examples. For example, dosages from 500 um to 2 mg per administration per mouse (weighing approx. 25-30 gm, most often approx. 30 gm) can be extrapolated for subjects of different weights such as primates especially humans using their weights and scaling accordingly.

Formulation

The component(s) of the present invention may be formulated into a pharmaceutical composition, such as by mixing with one or more of a suitable carrier, diluent or excipient, by using techniques that are known in the art.

Pharmaceutically Active Salt

The agent of the present invention may be administered as a pharmaceutically acceptable salt. Typically, a pharmaceutically acceptable salt may be readily prepared by using a desired acid or base, as appropriate. The salt may precipitate from solution and be collected by filtration or may be recovered by evaporation of the solvent.

Treatment

It is to be appreciated that all references herein to treatment include one or more of curative, palliative and prophylactic treatment. Preferably, the term treatment includes at least curative treatment and/or prophylactic treatment.

The treatment may be of one or more of prion disease (including prion infection), or related complaint.

Therapy

The agents of the present invention may be used as therapeutic agents—i.e. in therapy applications.

As with the term "treatment", the term "therapy" includes curative effects, alleviation effects, and prophylactic effects.

The therapy may be on humans or animals.

The therapy can include the treatment of one or more of prion disease/prion infection, or related complaint.

Sequence Homology

Fragments, mutants, alleles and other derivatives of the sequences of interest preferably retain substantial homology with said sequence. As used herein, "homology" means that the two entities share sufficient characteristics for the skilled person to determine that they are similar. Preferably, homology is used to refer to sequence identity. Thus, the derivatives of the sequences of interest preferably retain substantial sequence identity with said sequence.

Thus the present invention also relates to agents such as antibodies having CDR sequences homologous to those presented in the sequence listing, and to the uses of such antibodies and to methods involving their use as described herein.

In the context of the present invention, a homologous sequence is taken to include any sequence which is at least 60, 70, 80 or 90% identical, preferably at least 95 or 98% identical over at least 5, preferably 8, 10, 15, 20, 30, 40 or even more residues or bases with the sequence of interest, for example as shown in the sequence listing herein. In particular, homology should typically be considered with respect to those regions of the sequence of interest which may be known to be functionally important ie. the complementarity determining regions (CDRs) rather than non-essential neighbouring sequences such as framework regions, except of course where framework residues contribute to complementarity when such residues would be regarded as functionally important also. Homology comparisons can be conducted by eye, or more usually, with the aid of readily available sequence comparison programs. In some aspects of the present invention, no gap penalties are used when determining sequence identity.

Relative sequence identity may be determined by computer programs which can calculate the percentage identity between two or more sequences using any suitable algorithm for determining identity, using for example default parameters. A typical example of such a computer program is CLUSTAL (see Thompson et al., 1994 (NAR 22: 4673-80). Advantageously, the BLAST algorithm is employed, with parameters set to default values. The BLAST algorithm is described in detail at the Pubmed NIH website. Other computer programs used to determine identity and/or similarity between sequences include but are not limited to the GCG program package (Devereux et al 1984 Nucleic Acids Research 12: 387), FASTA (Atschul et al 1990 J Mol Biol 403-410) and the GENEWORKS suite of comparison tools. Preferably, sequence comparisons are conducted using the simple BLAST search algorithm.

Although in general the techniques mentioned herein are well known in the art, reference may be made in particular to Sambrook et al., Molecular Cloning, A Laboratory Manual (1989) and Ausubel et al., Short Protocols in Molecular Biology (1999) $4^{th}$ Ed, John Wiley & Sons, Inc.

EXAMPLES

General Methods:

Inoculation of FVB/N mice with RML prion inoculum. Rocky Mountain Laboratory (RML) prions were passaged in FVB/N mice and prion inoculum was prepared from the brains of terminally sick mice (incubation time to terminal scrapie, 153±4 days). Brains were homogenised in PBS (10% wt/vol) with 1% BSA using a Ribolyzer (Hybaid). The homogenate was spun for 5 min at 500×g and supernatants pooled and frozen at −80° C. until use. The infectious titre of the pooled homogenate was determined as 8.1 log $LD_{50}$/g brain by infectivity assay with tga20 indicator mice[26]. FVB/N mice were inoculated intracerebrally with 30 μl or intraperitoneally with 100 μl of 1% homogenate.

Infectivity bioassays. Assays were performed on 1% spleen homogenates. 30 μl aliquots were inoculated intracerebrally into groups of 3 or 4 tga20 mice per spleen, three or four spleens per treatment regimen. Incubation time to terminal scrapie sickness was determined and infectivity titres were calculated by using the equation y=11.45-0.088×(for RML 4.1), where y is the infectious titre (Log $LD_{50}$), and x is the incubation time (in days) to terminal disease[26].

Figure 4:
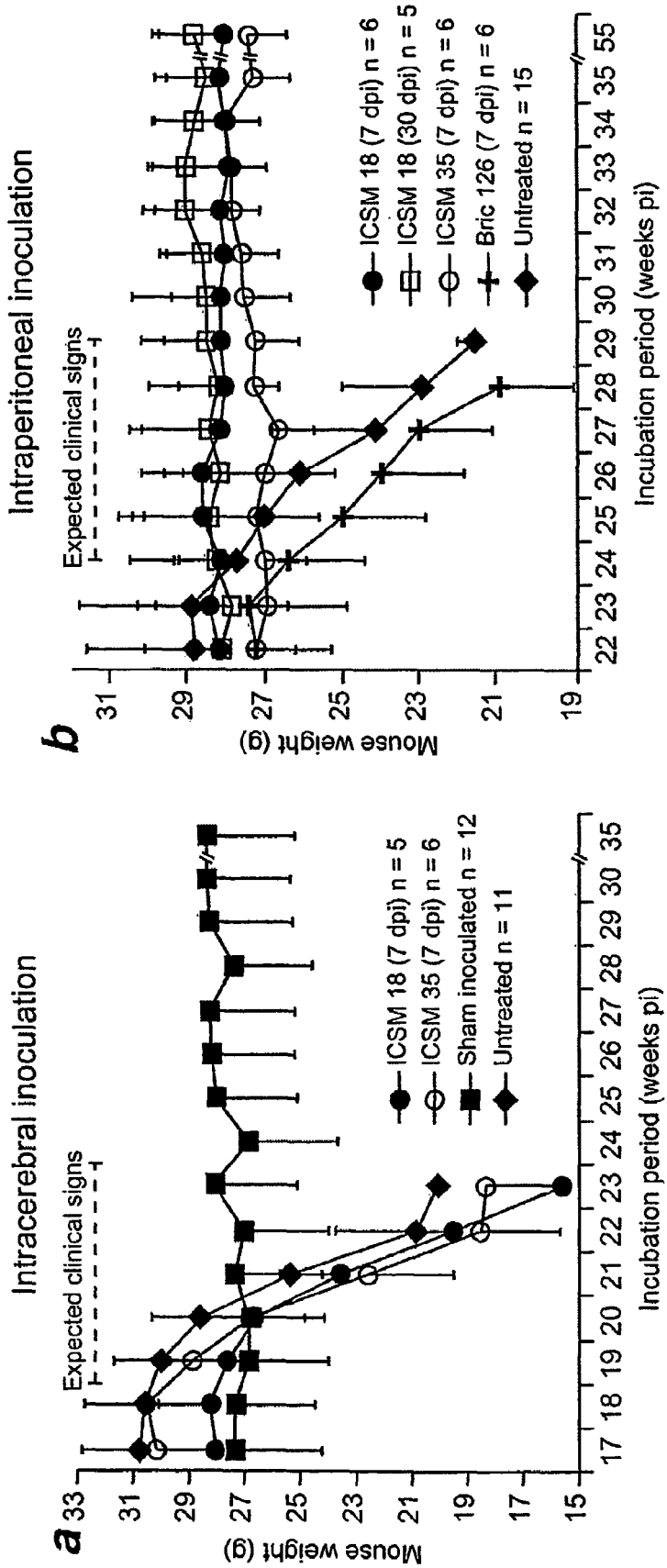
FIG. 4. Mice were weighed weekly from 17 weeks (panel a) or 22 weeks (panel b) after intracerebral or intraperitoneal scrapie inoculation. Weight loss was evident-after intracerebral inoculation in all mice except the PBS-inoculated group, but not in mice passively immunised with ICSM 18 or ICSM 35 from 7 or 30 days post intraperitoneal inoculation (dpi) of RML scrapie prions. Untreated and BRIC 126-treated mice steadily lost weight from 22 weeks pi until death from terminal scrapie sickness (untreated; 197±5 days pi, BRIC 126; 195±7 days pi) (confirmed by $PrP^{Sc}$ Western blot).

Passive immunisation. Groups of mice were injected twice weekly via intraperitoneal route with 2 mg (unless otherwise stated) of ICSM 18, ICSM 35, $IgG_1$ isotype control (BRIC 222 recognising CD44[27]) or $IgG_{2b}$ isotype control (BRIC 126 recognising CD47[28]) mAbs in PBS. Animals were monitored daily for clinical symptoms of scrapie[29] and weighed weekly from 17 weeks after ic inoculation or 22 weeks after ip inoculation. Clinical signs in untreated mice were first observed approximately 4 weeks prior to terminal illness (day of death) and included coat ruffling/discolouration, progressive weight loss, bradykinesia (slow movement), tail rigidity, dystonia (clasp foot), kyphosis (hunched back), ataxia and stupor. Weights of scrapie-infected (untreated) mice decreased prior to terminal illness from 3 and 4 weeks respectively in ic and ip-inoculated mice (FIG. 4). Confirmation of scrapie disease was performed by Western blot analysis of $PrP^{Sc}$ in brain tissue and in some cases by standard PrP immunohistochemistry.

Immunoprecipitation. Immunoprecipitation of PrP from murine brain tissues using ICSM and BRIC antibodies was performed as described.

Western-blot analysis. Spleens were homogenised in PBS to 10% w/v and $PrP^{Sc}$ was precipitated from 500 μl of homogenates using sodium phosphotungstic acid (NaPTA) as previously described[30]. $PrP^{Sc}$ pellets were resuspended in 20 μl of 2% sarkosyl buffer, treated with proteinase K (50 μg/ml, 50 min, 37° C.), boiled in sample buffer (5 min) and 15 μl aliquots (equivalent to ~2 mg of spleen homogenate) were electrophoresed through 16% SDS-PAGE gels. Brain homogenates were diluted to 1% (wt/vol) in PBS, treated with proteinase K (50 μg/ml for 60 min, 37° C.) and electrophoresed as for spleens. Proteins were transferred to PVDF membrane by semi-dry blotting, blocked with TBST/5% non-fat milk, incubated with biotinylated ICSM 18 (0.1 μg/ml) and developed by Enhanced Chemiluminescence (Amersham). Semi-quantitation was performed by densitometric analysis using MacBas version 2.5 software. At least 3-4 mice were examined from each treatment group. Bars on graphs are standard deviations. To standardise the $PrP^{Sc}$ signal between blots, 10 μl of $PrP^{Sc}$ precipitated from pooled spleens of terminal (Ter) scrapie-affected mice was loaded on each gel. Densitometric measurement of $PrP^{Sc}$ from treated and untreated spleens was compared to the standard $PrP^{Sc}$ sample and adjusted to relative intensities.

Histology and immunohistochemistry. For PrPSC immunohistochemistry, spleens and brains were fixed in 10% formalin. Prion infectivity was inactivated by immersion in 98% formic acid and postfixed in formalin for 24h. Tissues were dehydrated in graded alcohols and xylene, embedded in paraffin, sections cut at 3 urn nominal thickness and stained with hematoxylin & eosin. After antigen retrieval by microwaving for 15 mm, sections were immunostained with biotinylated ICSM 18 or ICSM 35 on a Ventana automated staining apparatus Ventana, Medical Systems, Inc., Tucson. Ariz.). For immune cell staining, spleens were frozen on dry ice in OCT. Air dried, frozen sections (8-10 urn) were fixed in acetone for 10 mm, air dried for 15 mm and endogenous peroxidases inactivated for 10 mm with 0. 1% H202. After washing in PBS, sections were immunostained for the follicular dendritic cell marker, FDO-M1 (1: 50), T lymphocytes, CD4 and CD8a or B lymphocytes, CD19 (all at 1: 100, purchased from Pharmingen) and visualized by incubation with biotinylated goat anti-rat IgG (1:50) and horseradish peroxidase (HRP)-labelled streptavidin/DAB. Sections were counterstained with Haematoxylin and mounted for microscopic observation.

ELISA of ICSM antibodies in mouse serum. 96 well ELISA plates were coated with recombinant mouse alpha $Prp^{90-231}$ (10 μg/ml) in ELISA coating buffer (35 mM sodium bicarbonate, 15 mM sodium carbonate, pH 9.4) and incubated for 1 h at 37° C. Plates were washed three times with PBS plus 0.05% Tween 20 (PBST), blocked with 10% fetal calf serum in RPMI medium and incubated with 50 μl of serially diluted mouse sera samples for 1 h at 37° C. After three washes, a 1/5000 dilution of a horseradish-peroxidase (HRP) conjugated anti-mouse IgG (Sigma) was added for 30 min at 37° C. and washed a further three times. The plates were developed with OPD buffer prior to spectrophotometric analysis (490 nm). Serially diluted ICSM 35 or ICSM 18 was measured in parallel to construct standard curves.

Example 1

Production of Agents for Use in Prion Inhibition

Recombinant human $PrP^{91-231}$ folded into either alpha or beta conformations[8,9] was used to produce monoclonal antibodies in $Prnp^{0/0}$ mice[10] that are intolerant of $PrP^c$.

ICSM 35, an IgG$_{2b}$ mAb raised against beta-PrP, with high affinity for both murine PrP$^c$ and PrP$^{Sc}$ (FIG. 1a) recognises a region between amino acid residues 91-110.

Figure 1:
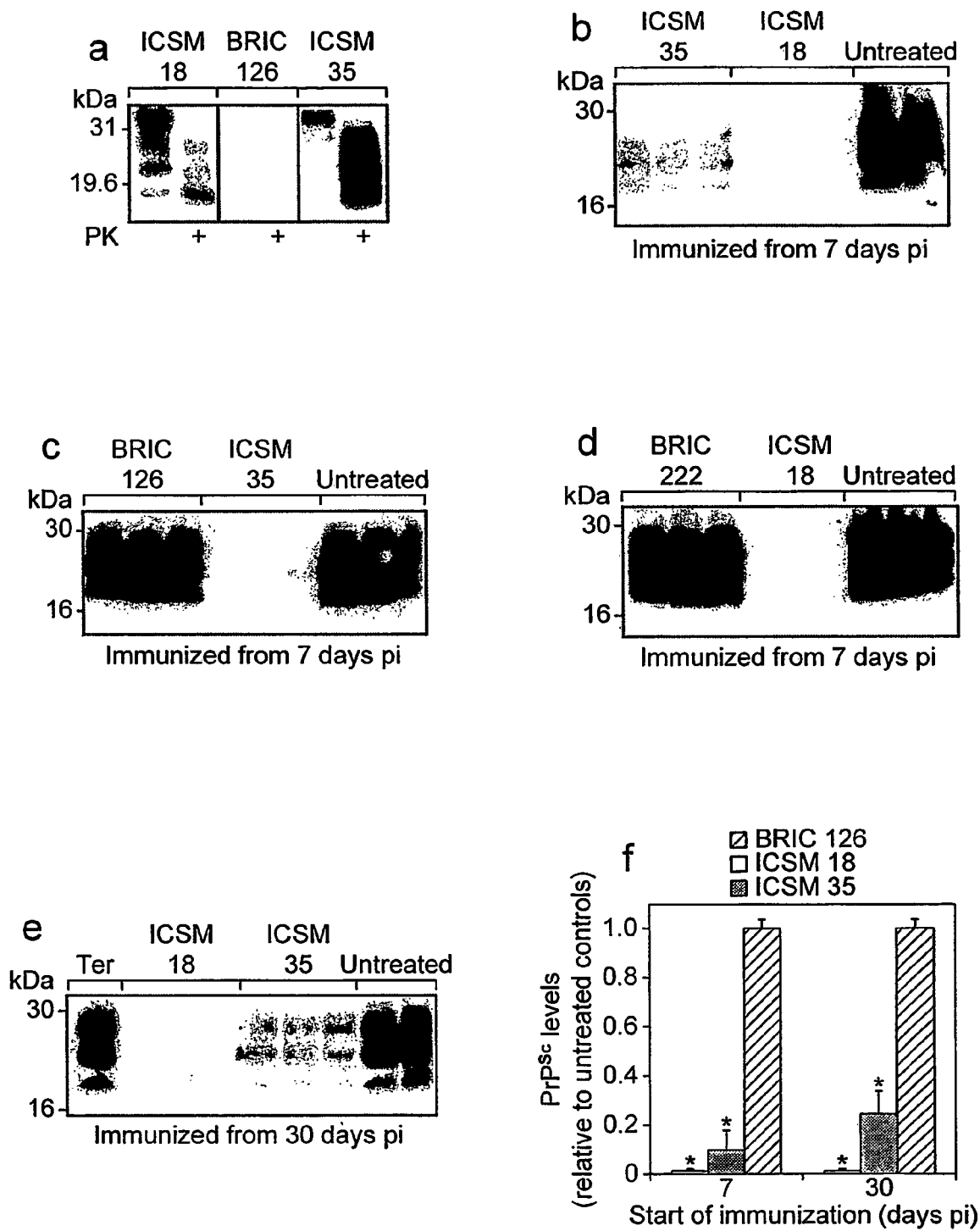
FIG. 1: Western blots of Proteinase K-digested, phosphotungstic acid-precipitated $PrP^{Sc}$ from spleens of mice 60 days post infection (pi) with RML scrapie. Mice were inoculated intraperitoneally except in panel j. Each lane contains $PrP^{Sc}$ from an individual mouse. Ter; Pooled splenic $PrP^{Sc}$ from mice succumbing to terminal scrapie (195±5 days pi). a, Immunoprecipitation of PrP from scrapie-infected mouse brain using ICSM or BRIC antibodies. PK; proteinase K. b-e, ICSM 18 and ICSM 35 induced substantial reductions in splenic $PrP^{Sc}$ levels when treatment began from 7 or 30 days pi. f, Densitometry of $PrP^{Sc}$ in Western blots. ICSM 18 induced greater reduction in $PrP^{Sc}$ levels in spleens than ICSM 35 while BRIC 126 had no effect (*P<0.001 compared to untreated spleens). g, ICSM 18 efficiently cleared $PrP^{Sc}$ whether treatment began at 7 or 30 days pi. h, ICSM 18 induced a dose-dependent reduction in $PrP^{Sc}$ levels in spleens as determined by densitometry of Western blots (*P<0.001, ANOVA compared to control antibody treatment). i, ICSM 35 induced more efficient inhibition of $PrP^{Sc}$ accumulation when treatment began at 7 days rather than 30 days pi. j, ICSM 18 and ICSM 35 inhibited $PrP^{Sc}$ accumulation in intracerebrally inoculated mice.
Figure 1:
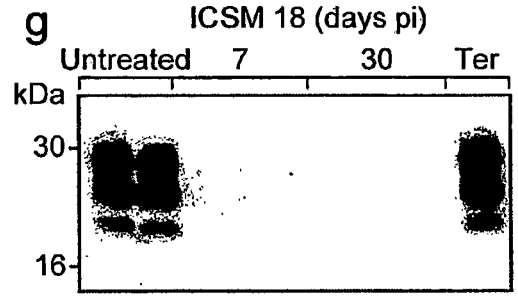
Figure 1:
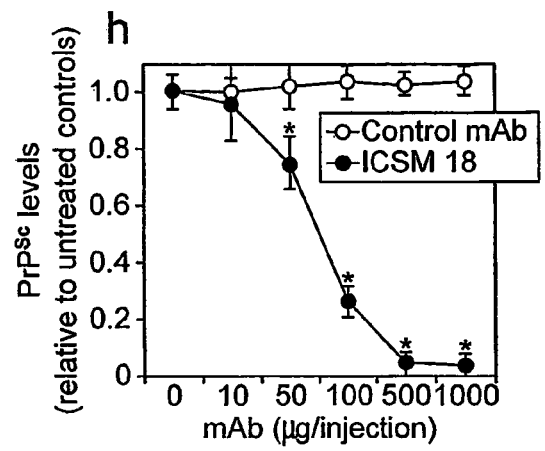
Figure 1:
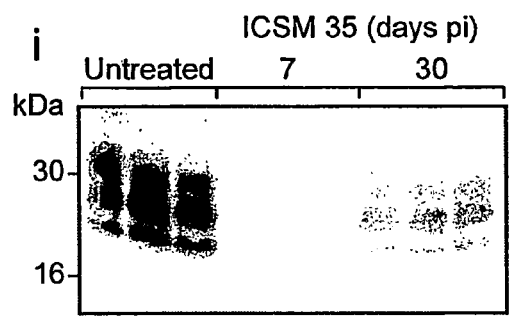
Figure 1:
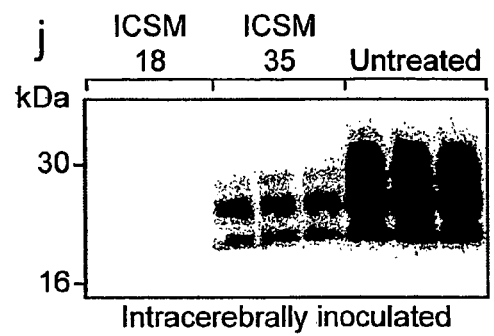

ICSM 18 (isotype IgG$_1$), raised against alpha-PrP, recognises residues 146-159 of murine PrP and has a lower affinity for PrP$^{Sc}$ (FIG. 1a).

Production of monoclonal antibodies. ICSM 35 and ICSM 18 monoclonal antibodies were produced. ICSM and BRIC mAbs were identically affinity-purified from culture supernatant, concentrated, and stored as sterile solutions without vehicle protein at 4° C. MAbs were used undiluted or diluted in PBS prior to use in vivo.

Example 2

Use of Anti-PrP Antibodies in Prion Inhibition in Vivo

FVB/N mice were challenged intraperitoneally (ip) with RML scrapie brain homogenate derived from terminally scrapie-sick mice and treated with ICSM 35, ICSM 18 or isotype control antibodies BRIC 126 ($IgG_{2b}$) and BRIC 222 ($IgG_1$) by twice weekly ip injection (2 mg per injection) from 7 or 30 days post inoculation (pi).

ELISA of ICSM Antibodies in Mouse Serum

Serum levels of ICSM 35 and ICSM 18 treated mice (4 mice/group) were quantitated by ELISA 30 days after commencing twice weekly 2 mg intraperitoneal injections. Serum ICSM 35 and ICSM 18 levels 4 days after the last treatment were 460±50 and 398±38 μg/ml respectively (mean±SD). The difference was not significant ($P<0.10$, ANOVA).

Thus, ELISA analysis after 30 days of mAb treatment revealed no significant differences between ICSM 35 or ICSM 18 mAb levels in the serum.

Western blots of Proteinase K-treated, phosphotungstic acid-precipitated $PrP^{Sc}$ from spleens of mice at 60 days pi revealed that treatment from 7 days pi with ICSM 35 or ICSM 18, but not with BRIC antibodies, dramatically inhibited $PrP^{Sc}$ accumulation in the spleen (FIG. 1*b-d*).

Time-course analysis of peripheral $PrP^{Sc}$ accumulation in mice confirmed that $PrP^{Sc}$ was detectable in the spleen at 7 days and plateaued by 30-40 days after peripheral challenge as previously reported[12].

Treatment of scrapie-infected mice with ICSM 35 or ICSM 18 from 30 to 60 days pi resulted in a substantial reduction in splenic $PrP^{Sc}$ levels when compared to untreated controls or to mice treated with isotype control antibody (FIG. 1*e*).

ICSM 18 reduced $PrP^{Sc}$ levels by 99±1% and 96±3% (mean plus/minus standard deviation, *$P<0.001$, analysis of variance (ANOVA)) after treatment from 7 or 30 days pi respectively (FIG. 1*f*). ICSM 35 also lowered $PrP^{Sc}$ levels by 90±8% and 75±3% (*$P<0.001$, ANOVA) for the same treatment periods, while isotype control antibody did not alter $PrP^{Sc}$ levels (FIG. 1*f*). Immunoblots probed with ICSM 35 instead of ICSM 18 as the primary antibody produced indisinguishable results.

Treatment of mice from 7 or 30 days pi with ICSM 18 consistently resulted in almost complete loss of detectable $PrP^{Sc}$ in spleens by Western blot (FIG. 1*g*) and this effect was dose-dependent (FIG. 1*h*). ICSM 35 treatment from 7 days pi reduced splenic $PrP^{Sc}$ levels with similar efficiency to ICSM 18.

When ICSM35 treatment began at 30 days pi, inhibition of $PrP^{Sc}$ replication was substantial, but possibly incomplete (FIG. 1*i*). This may reflect differences in affinity or avidity of ICSM 35 and ICSM 18 for normal and disease-related PrP as shown in FIG. 1*a*.

Analogous results were obtained when intracerebrally inoculated (ic) mice were treated with ICSM 18 or ICSM 35 (FIG. 1*j*). As ICSM 18 recognizes the PrP epitope 146-159, these data are consistent with residues 132-156 incorporating helix 1 of mouse PrP having a crucial role in prion replication[6-7,13-15].

Tissue sections derived from formalin-fixed spleens at 60 days pi were examined by standard PrP immunohistochemistry using ICSM 18 and ICSM 35 (FIG. 2*a-h*). Both mAbs were applied to adjacent splenic sections to ensure that antibody bound in vivo did not spuriously block the detecting mAb. ICSM 18 produced weak staining of $PrP^{Sc}$ in spleens from untreated, scrapie-infected mice (FIG. 2*a*), while ICSM 35 revealed intense labelling of $PrP^{Sc}$, primarily associated with germinal centres (FIG. 2*e*).

$PrP^{Sc}$ immunostaining was substantially reduced in spleens of ICSM 18 and ICSM 35-treated mice when labelled with either ICSM 18 (FIGS. 2*b* and *c*) or ICSM 35 (FIGS. 2*f*, 2*g* and 5) as primary antibody.

Quantitation of $PrP^{Sc}$ Germinal Centres in ICSM Antibody Treated Mice

The number of $PrP^{Sc}$-positive germinal centres derived from each spleen was quantitated (blinded to the treatment). At least 6 sections from 3 spleens were examined from each treatment group. ICSM 35 staining revealed that 24±10% (mean±SD) of germinal centres were $PrP^{Sc}$-positive in untreated (positive control) spleens and this fell to 1±3% and 3±4% in ICSM 35 and ICSM 18-treated spleens respectively ($P<0.0005$, ANOVA). Analogous reductions in $PrP^{Sc}$-positive germinal centres were observed after staining with ICSM 18.

As expected, $PrP^{Sc}$-positive germinal centres were not seen in splenic sections from mice unchallenged with RML prions (FIG. 2*d* and *h*). Bioassay of splenic homogenates from ICSM 35 and ICSM 18-treated mice showed respectively a 1.5-3.5 and >4 log reduction in infectious titres compared to controls (Table 1).

Example 3

Treatment/Prevention of Prion Disease in Subjects

Evidence for accompanying clinical benefit is presented in this Example.

Treatment is effective if begun before the onset of clinical scrapie (Table 1).

Mice that were inoculated intraperitoneally with RML scrapie and treated with ICSM 35 or ICSM 18 (2 mg twice weekly) from 7 and 30 days pi continue to survive for much longer than untreated mice or mice treated with isotype control antibody (Table 1).

The mean survival for untreated ip inoculated mice was 197±5 days. All mice treated with ICSM 18 or ICSM 35 from 7 or 30 days post ip challenge have survived for more than 400 days pi at the time this manuscript was prepared (Table 1); an extension of the incubation period by at least 100% ($p<0.001$, ANOVA). No clinical signs of scrapie (as described in the Methods section) or weight loss (FIG. 4) have yet been observed in these mice.

Mouse Body Weights in ICSM Antibody Treated and Control Mice

Untreated intracerebrally and intraperitoneally inoculated mice developed classical signs of scrapie (see Methods section for clinical signs) including progressive weight loss until death (FIGS. 4*a* and *b*). Treatment with ICSM 18 or ICSM 35 failed to prevent weight loss in ic-inoculated animals (FIG. 4*a*). In contrast, ip-inoculated mice treated with ICSM 18 or ICSM 35 have not yet shown any clinical signs (>400 days) or lost weight (>385 days) after the RML challenge (FIG. 4*b*). Body weights of untreated mice and mice treated with isotype control antibody dropped significantly (average of 7.4 grams per mouse at time of death, P<0.007, ANOVA compared to ICSM treated mice) from day 154 pi until death from scrapie (FIG. 4b).

Thus the present invention provides methods for the treatment and prevention of prion disease.

Figure 5:
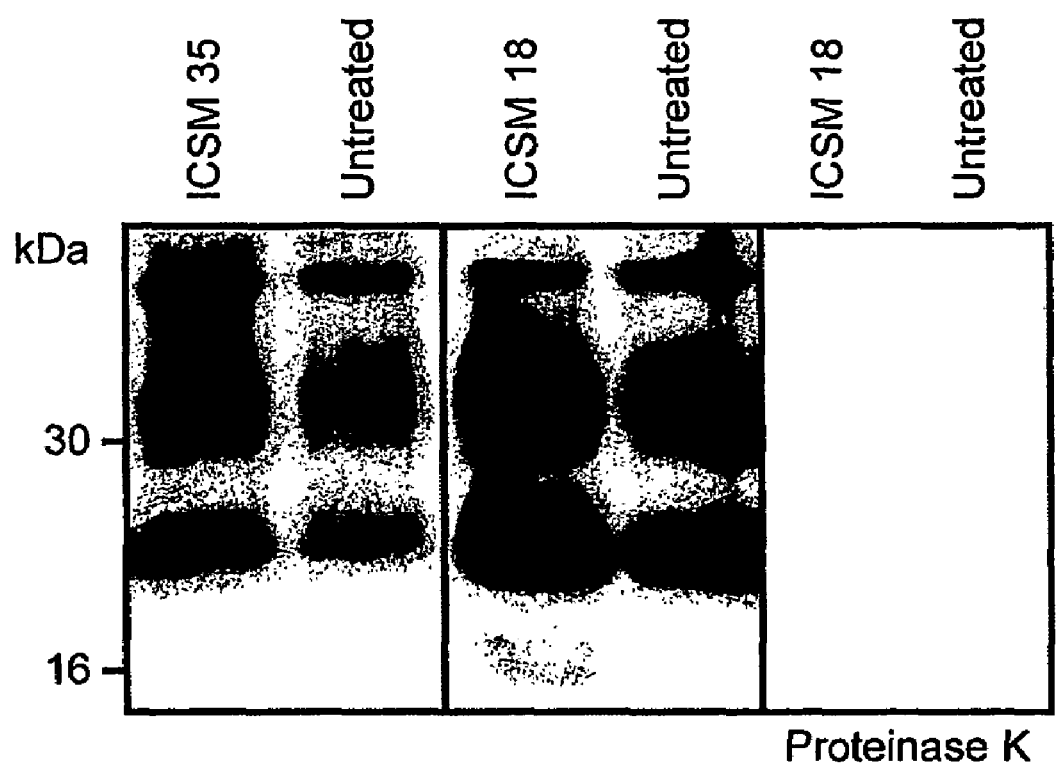
FIG. 5. $PrP^c$ immunostaining in spleen samples from mice treated for 30 days with 2 mg of ICSM 35 or ICSM 18 administered twice weekly via the intraperitoneal route. Whole spleen (2 μl of a 10% homogenate) derived from individual treated or untreated mice was immunoblotted and $PrP^c$ detected using biotinylated ICSM 18. Each lane is derived form a single mouse and is representative of the three mice in each group.

Tissues were examined from ip-inoculated mice treated with ICSM 18 or ICSM 35 from 7 days pi and lacking signs of clinical scrapie (sacrificed 250 days pi). Here PrP$^{Sc}$ was undetectable in the brain after either treatment and only low levels of PrP$^{Sc}$ were seen in spleens of ICSM 35-treated mice (FIG. 3a-d). No reduction in PrP$^c$ immunostaining was observed in spleen samples from mice treated with ICSM 35 or ICSM 18 when compared to untreated controls (FIG. 5).

This illustrates the effectiveness of the invention in inhibiting prion replication in vivo.

Similarly, no PrP$^{Sc}$ was observed in the brain after ICSM 35 treatment from 30 days pi and analysed at 230 days pi. High levels of PrP$^{Sc}$ were observed in brains and spleens from BRIC antibody-treated and untreated mice that succumbed to scrapie after ip inoculation (FIG. 3a-d). These findings were confirmed by histopathological analysis and bioassay of infectivity from these tissues is in progress.

Example 4

Inhibition of Prion Replication

This Example illustrates inhibition of prion replication according to the present invention. It is further demonstrated that this effect is due to inhibition of prion replication rather than a general loss of PrP.

We examined if passive immunisation with anti-PrP mAbs affected immune cell populations as targeted depletion of PrP[30] cell-types could theoretically have contributed to loss of PrP$^{Sc}$ detection in spleens of antibody treated mice described in Example 3[16,17].

Flow Cytometry

Splenic T-cell and B-cell populations were analysed by flow cytometry (Table 2). No significant differences were observed in percentages of T and B cell populations from mice treated with ICSM 35 or ICSM 18 when compared to BRIC antibody controls (Student's paired t-test).

TABLE 2

Flow cytometric analysis of splenic T and B cell populations from mice treated with ICSM 35 or ICSM 18.

| Antibody treatment[a] | CD3$^+$ (%)[b] | CD19$^+$ (%) |
|---|---|---|
| Untreated | 42.8 ± 3.4 | 43.4 ± 4.1 |
| ICSM 18 | 48.7 ± 3.0 | 37.6 ± 2.6 |
| ICSM 35 | 48.1 ± 3.9 | 40.1 ± 3.6 |
| Bric 126 | 46.0 ± 5.0 | 41.1 ± 5.9 |
| Bric 222 | 47.6 ± 5.1 | 37.0 ± 4.6 |

[a]Mice (n = 4/group) were treated with 2 mg of ICSM or BRIC antibodies twice weekly for 30 days.
[b]Splenocytes were harvested and single cell suspensions made by gentle dispersion. Aliquots of 2 × 10$^5$ cells from each spleen were incubated with saturating amounts of directly conjugated anti-CD19-fluorescein isothiocyanate and anti-CD3-phycoerythrin (both IgG$_1$) (Pharmingen, UK) and analysed by flow cytometry on a FACS Calibur instrument (Becton Dickinson, UK). The proportion of B cells (CD19$^+$) and T cells (CD3$^+$) in gated splenic mononuclear cell populations was determined using CellQuest software and the significance of the observed differences analysed by ANOVA. <1% of the cells were double positive.

Figure 3:
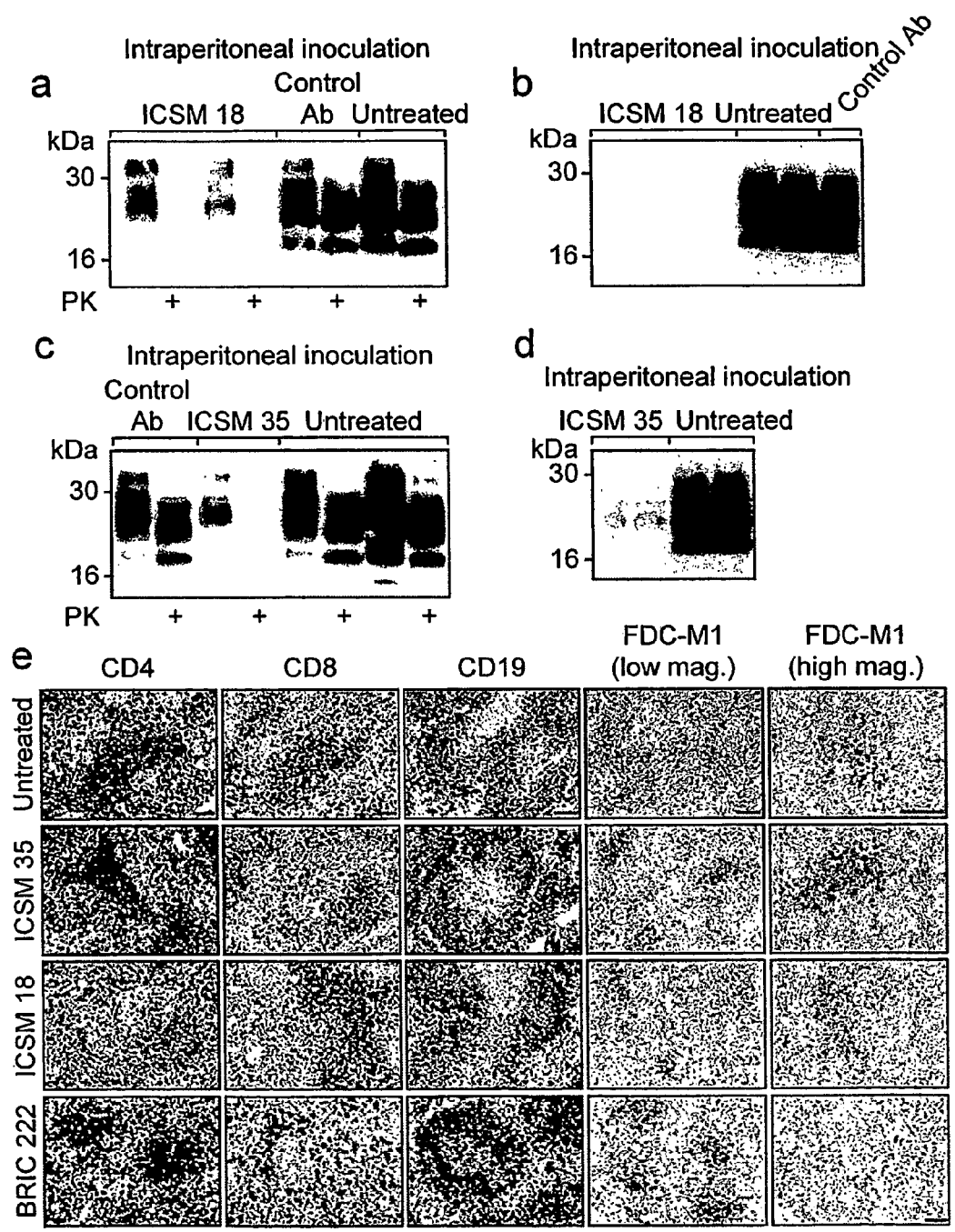
FIG. 3: a-d, Western blots of $PrP^{Sc}$ in brain homogenates (a and c) or Proteinase K treated, phosphotungstic acid precipitated PrP from spleens (b and d). $PrP^{Sc}$ levels were absent (a-c) or significantly reduced (d) in brain and spleen of mice treated with ICSM 18 or ICSM 35 from 7 days pi and sacrificed 250 days pi. BRIC control antibody (Ab) treated mice succumbed to scrapie after 195 days pi. PK; Proteinase K. e, Immunohistochemical analysis of splenic immune cell populations. Frozen spleen sections from mice 60 days pi were immunostained (brown deposits) with antisera against T-lymphocytes (CD4 or CD8), B-lymphocytes (CD19) or follicular dendritic cells (FDC-M1). No differences were observed in FDC or lymphocyte populations between untreated, ICSM 35, ICSM 18 and BRIC 222 treated mice (treated from 7 days pi). The far right-hand column shows higher magnification (high mag.) panels of the germinal centres in the adjacent column (low mag.). The BRIC 222 photomicrograph of the far right-hand column represents no primary antibody control. Bar=100 μm.

No differences were observed in splenic T and B cell populations between untreated scrapie-inoculated mice and antibody-treated mice (examined at 60 days pi) as determined by immunostaining of cryostat tissue sections (FIG. 3e, see also Table 2).

Follicular dendritic cells (FDCs) are an important site of PrP$^{Sc}$ accumulation following peripheral prion infection[17,18]. Immunostaining of splenic sections from untreated mice revealed FDC-M1$^+$ cells scattered throughout the germinal centres or in small clusters within the germinal centre (FIG. 3e). In contrast, ICSM or BRIC antibody-treated spleens often revealed larger numbers of FDC-M1$^+$ cells clustered tightly within the germinal centre (FIG. 3e). These data clearly show that prolonged treatment with the anti-PrP antibodies does not induce deletion of the FDC cell-type within the spleen and demonstrate that the substantial reduction in PrP$^{Sc}$ levels observed in spleens treated with anti-PrP mAbs is due to direct inhibition of PrP$^{Sc}$ production. This is further illustrated by unaltered PrP$^c$ immunoblotting in spleen homogenates from mice treated with ICSM 35 or ICSM 18 (FIG. 5).

Example 5

Epitope Mapping and Further Detailed Methods

Outline:

Prion diseases are a group of invariably fatal neurodegenerative disorders that include Creutzfeldt-Jakob disease in humans, scrapie in sheep and goats, and bovine spongiform encephalopathy in cattle. The infectious agent or prion is largely composed of an abnormal isoform (PrP$^{Sc}$) of a host encoded normal cellular protein, PrP$^c$. The conversion of PrP$^c$ to PrP$^{Sc}$ is a dynamic process and for reasons that are not clear, the distribution of spongiform change and PrP$^{Sc}$ deposition varies among prion strains. One explanation for this would be that the transformation efficiency in any given brain region depends on favourable interactions between conformations of PrP$^c$ and the prion strain being propagated within it. However identification of specific PrP$^c$ conformations has until now been hampered by a lack of suitable panels of antibodies that discriminate PrP$^c$ subspecies under native conditions. In this study, we show that monoclonal antibodies raised against recombinant human prion protein folded into alpha or beta conformations, exhibit striking heterogeneity in their specificity for truncations and glycoforms of mouse brain PrP$^c$. We then show that some of these PrP$^c$ isoforms are differentially expressed in certain mouse brain regions. This suggests that variation in the expression of PrP$^c$ conformations in different brain regions may dictate the pattern of PrP$^{Sc}$ deposition and vacuolation, characteristic for different prion strains.

The cellular prion protein (PrP$^c$) is almost ubiquitously expressed and conserved in several mammalian species (Oesch et al, 1991). Although the highest levels of PrP$^c$ are found in neurones (Bendheim et al, 1992), its precise physiological role remains unknown and transgenic mice devoid of PrP$^c$ (Prnp$^{0/0}$) have little phenotypic abnormality (Büeler et al, 1992). PrP$^c$ may have a physiological role in neuronal differentiation (Wion et al, 1988), synaptic transmission (Collinge et al., 1994) and recent work demonstrates its high affinity for copper (Jackson et al., 2001). PrP$^c$ is anchored at the cell surface by a carboxy-terminal glycosylphosphatidylinositol (GPI) moiety (Stahl et al., 1990). Two sites of non-obligatory Asn-linked glycosylation at residues 180 and 196 and a disulphide bond between cysteine residues at 178 and 213 have been identified in PrP$^c$ (Caughey, 1993). Mature and fully glycosylated mouse PrP$^c$ migrates at 33-35 kDa on electrophoretic gels and its unglycosylated counterpart at 27 kDa (Haraguchi et al., 1989). In human brain, 2 other amino-terminal truncated prion proteins have also been identified, resulting from endogenous proteolytic cleavage. Their unglycosylated forms migrate respectively at 18 kDa and 21-22 kDa (Jimenez-Huete et al, 1998).

Prion diseases are invariably fatal transmissible neurodegenerative disorders including scrapie in sheep and goats, bovine spongiform encephalopathy (BSE) in cattle, and Creutzfeldt-Jakob disease (CJD) in humans. The infectious agent or prion is mainly composed of $PrP^{Sc}$, a detergent-insoluble and protease-resistant isoform of $PrP^c$ (Prusiner, 1982). The acquisition of protease resistance is explicable by the post-translational and autocatalytic conversion of $PrP^c$ from a largely alpha-helical conformation into one rich in beta-sheet ($PrP^{Sc}$). Within species, the disease phenotype is not uniform and prion 'strains' can be differentiated on the basis of the incubation period and the neuropathological changes they induce in experimentally infected inbred mouse lines. Currently the prevailing view is that strain diversity is determined by variations in $PrP^{Sc}$ conformation or glycoform composition (Bessen and Marsh, 1994; Collinge et al., 1996; Telling et al., 1996). Neuropathologically, the precise regional variation in vacuolation and $PrP^{Sc}$ deposition suggests strain-specific targeting of particular neuronal populations (Bruce et al, 1994a). However it remains to be explained how, during prion propagation, $PrP^{Sc}$ selectively accumulates in some brain regions and not in others. An attractive hypothesis would be that alternative $PrP^{Sc}$ conformations interact more or less efficiently with subspecies or isoforms of $PrP^c$ differentially expressed in certain brain regions. The aim of this example therefore was to determine if such anatomical variation in the central nervous system (CNS) expression of $PrP^c$ isoforms exists.

Antibody Production

We first produced and characterised a new panel of monoclonal antibodies (mAbs) that exhibit differential affinity for truncated and glycosylated forms of native $PrP^c$, and then used them to study the anatomical distribution of these heterogeneous $PrP^c$ isoforms in fresh frozen sections of mouse brain. This work indicates that there are indeed qualitative differences in $PrP^c$ expression in normal brain lending support for the notion that such differences might dictate the pattern of $PrP^{Sc}$ deposition and vacuolation, characteristic of different prion strains.

Production of the ICSM Antibodies

All the experiments with mice have been performed in compliance with our institutional and HM Home Office guidelines. FVB-N $Prnp^{0/0}$ mice were subcutaneously immunised with 50-100 µg of human recombinant $PrP^{91-231}$ folded either into alpha (to produce ICSM 1 to 26) or beta (to produce ICSM 35) conformation (Jackson et al., 1999b) in adjuvant on days 0,21,42, and then finally boosted intraperitoneally on day 50 with 50 µg in PBS. Three days later the mice were culled and single cell suspensions of splenocytes were cryopreserved. These were later thawed and then fused with non-secreting NS0 cells using conventional technology and hybridomas were subsequently screened for reactivity to alpha or beta-PrP and to native PrP. Positive hybridomas were repeatedly cloned until stable.

Peptide ELISA

High binding ELISA plates were coated with 50 µl of a 10 µg/ml solution of overlapping 15- to 20-mer mouse and human PrP peptides in ELISA coating buffer (35 mM sodium bicarbonate, 15 mM sodium carbonate, pH 9.4). The plates were incubated for 1 h at 37° C. and then washed 3 times with phosphate-buffered saline (PBS)-0.05% tween. After blocking with RPMI supplemented with 10% fetal calf serum, 50 µl of the relevant mAb (as culture supernatant) was added for 1 h at 37° C. After 3 washes with PBS-tween, a 1/5000 dilution of a horseradish-peroxidase (HRP) conjugated anti-mouse IgG (Sigma, UK) was added for 30 min at 37° C. and washed a further 3 times. The plate was then developed with OPD buffer and the reaction was stopped with 3M sulfuric acid prior to spectrophotometric analysis.

Immunoprecipitation of Murine $PrP^c$

Brain tissues from three FVB/N and FVB/N $Prnp^{0/0}$ (Zurich I (Büeler et al., 1992)) mice were homogenised (10% wt/vol. in PBS) with a Dounce homogeniser, and centrifuged at 1000 xg. The supernatants were stored at −80° C. until further use. For immunoprecipitation, brain homogenates were diluted to 0.5% in lysis buffer (20 mM Tris-HCl pH 7.5, 150 mM sodium chloride, 1% Nonidet P40, 0.5% sodium deoxycholate) with a cocktail of protease inhibitors (Roche Biochemicals, UK). The solution was then incubated (1:1 dilution) with 10 µg/ml purified ICSM mAbs in PBS or with neat hybridoma supernatant for 2 h, at 4° C. on a rotator. Negative controls consisted of omitting the capture mAb or $IgG_1$ (28-14-8S, an anti-MHC H-2D$^b$ mAb (Ozato et al., 1980) and $IgG_{2b}$ isotype controls (Avent et al., 4988). The immune complexes were then adsorbed overnight to protein G-agarose beads (Roche Biomedicals, UK) at 4° C. on a rotator. The beads were then washed with high and low salt buffers according to the manufacturer recommendations. After the last wash, the beads were resuspended in Laemmli buffer (Laemmli, 1970), heated at 100° C. for 5 min to detach/denature the bound protein and the beads were pelleted and the supernatant was removed.

Sequential Immunoprecipitation of Mouse $PrP^c$

To deplete the brain homogenate from full-length $PrP^c$, 0.5% brain homogenate was incubated (1:1 dilution) with 50 µg/ml purified ICSM 35 (see results) for 3 h, at 4° C. on a rotator. The immune complexes were then adsorbed overnight to protein G-agarose beads at 4° C. on a rotator. The beads were then pelleted and $PrP^c$ fragments contained in the supernatant were immunoprecipitated (1:1 dilution) with 10 µg/ml purified ICSM mAbs or with supernatant before adsorption to protein G as described above.

Enzymatic Deglycosylation of Immunoprecipitated $PrP^c$

A 10-20 µl aliquot of the inmmunoprecipitated and subsequently denatured $PrP^c$ was digested with 1000 U of recombinant PNGase (New England Biolabs, UK) for 2h at 37° C., in 1% Nonidet P40 and the proprietary buffer. The deglycosylated proteins were then precipitated in 3 volumes of cold acetone and re-suspended in 10-20 µl Laemmli buffer.

Immunoblots

Immunoprecipitated protein (deglycosylated or not) samples were run on 12% polyacrylamide gels, electrotransfered onto PVDF membranes (Millipore, UK) and immunoblotted with 0.2 µg/ml of biotinylated ICSM 18 avoiding detection of the immunoprecipitating antibody. After several washes with PBS-Tween, a 1/10000 dilution of streptavidin-HRP (Sigma, UK) was added. Immunoreactivity was visualized with an enhanced chemiluminescence kit on autoradiographic films (ECL+, Amersham, UK). Biotinylated molecular weight markers (Amersham) were used to accurately correlate the electrophoretic mobility of the immunoprecipitate to its molecular weight.

Immunohistochemistry of Mouse $PrP^c$

Immunohistochemical studies were performed on five FVB/N and FVB/N $Prnp^{0/0}$ (Zurich I) mice. Mice were killed with an overdose of pentobarbital. The brains were rapidly removed, embedded in OCT compound and frozen on dry ice. 8 µm cryostat sections were cut, fixed in acetone for 10 min and air-dried. Endogenous peroxidase was inactivated for 30 min with a 0.3% $H_2O_2$ solution in methanol. After washing in PBS, non-specific antibody binding was blocked with normal goat serum for 30 min. The sections were then stained for 1 h with either 10 μg/ml ICSM mAbs or with neat hybridoma supernatant. These concentrations were optimised for specific binding using equivalent PrP null mouse sections. After washing in PBS, a 1/100 dilution of HRP-conjugated anti-mouse IgG (Sigma, UK) was added for 45 min. Peroxidase activity was revealed with 3,3'-diaminobenzidine tetrahydrochloride for 3-10 min (Sigma, UK). Sections were counterstained with haematoxylin (Harris, UK), mounted and covered for microscopic observation.

Nomenclature

Numbering of PrP residues corresponds to mouse PrP throughout the study.

Results

Epitope Mapping of the ICSM Monoclonal Antibodies

Figure 2:
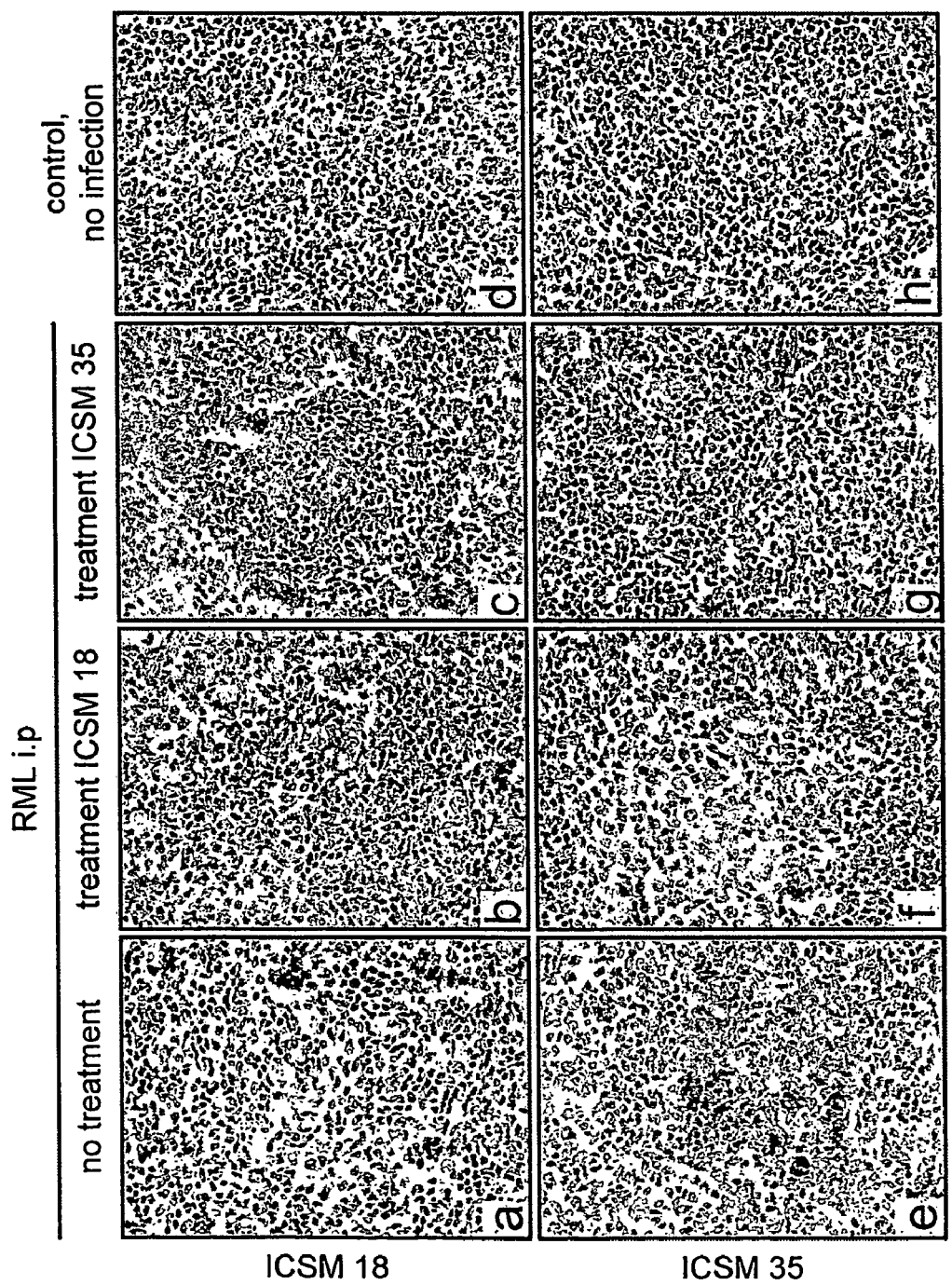
FIG. 2: a-h, Immunohistochemical staining of spleens with anti-PrP antibodies 60 days after intraperitoneal (i.p.) inoculation with RML scrapie: a, Spleen of a scrapie-infected mouse shows relatively weak PrP immunoreactivity with ICSM 18 in the follicular dendritic cells in several germinal centres. No PrP immunoreactivity in spleen after treatment of the animal with ICSM 18 (b) or ICSM 35 (c) or in uninoculated controls (d). e, Immunostaining with ICSM 35 reveals strong PrP immunoreactivity in follicle centres in spleens of scrapie-infected mice. f, After treatment with ICSM 18, very few follicles are immunoreactive for PrP and g, No positive follicles detectable after treatment with ICSM 35. No positive follicles in control spleens (h). Scale bar=100 µm.

ICSM 1 to 26 mAbs were raised in FVB/N Prnp$^{0/0}$ mice immunised with human recombinant PrP$^{91-231}$ produced in *E. coli* and refolded into a predominantly alpha-helical PrP$^c$-like conformation (Jackson et al., 1999a). ICSM 35 was obtained after immunisation with human recombinant PrP$^{91-231}$ refolded into a beta conformation (beta-PrP) (Jackson et al., 1999a). The epitopes of all of these mAbs must therefore lie within codon 91 and 231 (FIG. 1A). To further define these, peptide ELISA was performed with overlapping mouse and human 15- to 20-mer peptides covering this sequence. It showed that ICSM 18 bound strongly to peptide 146-159, a central region encompassing the first a helix of PrP$^c$ (Riek et al., 1996). ICSM 15 and 17 recognised a similar region, between residues 140 and 159 although ICSM 15 does not recognise murine PrP$^c$ (FIG. 2F). ICSM 35 recognised a peptide between residues 96 and 109 (FIG. 1A). None of the other ICSM mAbs used in this study recognised synthetic peptides absorbed to ELISA plates or inhibited mAb binding to recombinant protein in competition assays, suggesting that their epitopes are conformation-dependent.

SUMMARY OF EXAMPLES

It is disclosed herein for the first time that substantial peripheral prion replication can be effectively suppressed by passive immunisation. Importantly, treatment began well after the onset of peripheral prion replication and in the case of the 30 days pi treatment group, during the plateau phase of PrP$^{Sc}$ accumulation [12]. Continued treatment has delayed onset of scrapie by more than 100% of the usual incubation period in wild type FVB/N mice, illustrating effective treatment/prevention of prion disease according to the present invention. In contrast, previous therapeutic interventions only show benefit if treatment is begun prior to, or immediately after the day of inoculation[19-24] reflecting simple neutralisation of the inoculum as opposed to the inhibition of prion replication according to the present invention.

It is possible that passive transfer of these anti-PrP antibodies has reduced effect late in the incubation period when clinical signs have developed or in ic-inoculated subjects, most likely reflecting inadequate translocation of anti-PrP antibody across the blood-brain barrier (BBB)[25]. Blood-brain transport of the agents of the present invention is discussed above in the 'administration' section.

Furthermore, we found no evidence for autoimmune reactions in subjects. If any such problems should be encountered for example when treating humans with CJD or other prion diseases with humanized forms of these and/or other anti-PrP monoclonal antibodies, immunosuppressant strategies may be adopted without departing from the spirit or scope of the invention.

TABLE 1

Effect of passive immunisation with ICSM mAbs on spleen infectivity and survival of FVB/N mice inoculated with RML scrapie.

| IC or IP Inoculation[a] | Antibody Treatment[b] | Start of treatment (days pi) | Spleen Bioassay[d] | | FVB/N Mice succumbing to scrapie (n/n$_o$) | Mean survival time (days pi) |
|---|---|---|---|---|---|---|
| | | | Mortality: tga20 mice succumbing to scrapie (n/n$_o$)[e] | Spleen Titre: Mean Log LD$_{50}$ Infectious Units/ml 10% homogenate | | |
| IC | ICSM 35 | 7 | | | 6/6 | 152 ± 7 |
| IC | ICSM 35 | CO[c] | | | 8/8 | 148 ± 10 |
| IC | ICSM 18 | 7 | | | 5/5 | 151 ± 2 |
| IC | ICSM 18 | CO | | | 7/7 | 149 ± 3 |
| IC | BRIC 126 | 7 | | | 5/5 | 147 ± 4 |
| IC | None | — | | | 11/11 | 151 ± 7 |
| IP | ICSM 35 | 7 | 15/15 | 3.5 (2.7-4.3)[f] | 0/6[g] | >400 |
| IP | ICSM 35 | 30 | | | 0/5 | >400 |
| IP | ICSM 35 | CO | | | 6/6 | 193 ± 4 |
| IP | ICSM 18 | 7 | 3/12 | <1.5 | 0/6[g] | >400 |
| IP | ICSM 18 | 30 | 1/10 | <1.5 | 0/5 | >400 |
| IP | ICSM 18 | CO | | | 5/5 | 193 ± 5 |
| IP | BRIC 126 | 7 | 9/9 | 6.0 | 6/6 | 195 ± 7 |
| IP | BRIC 126 | 30 | | | 4/4 | 198 ± 4 |
| IP | None | — | 13/13 | 6.0 | 15/15 | 197 ± 5 |

[a]The infectious titre of the pooled RML scrapie brain homogenate was determined as 8.1 log LD$_{50}$/g brain by infectivity assay with tga20 indicator mice[26]. FVB/N mice were inoculated intracerebrally (IC) with 30 μl or intraperitoneally (IP) with 100 μl of 1% homogenate.
[b]Twice weekly until 375 days pi, then once per week, 2 mg per injection.
[c]CO, treatment began at clinical onset (as described in Methods section); 129-136 days pi (ic inoculated mice) and 168-177 days pi (ip inoculated mice)
[d]Determined at 60 days post infection of passively immunised and untreated FVB/N mice.
[e]n/n$_o$, number of animals succumbing to scrapie/number of animals inoculated.
[f]Range of Log LD$_{50}$ infectious units/ml 10% homogenate.
[g]Three ICSM 18-treated and two ICSM 35-treated mice (all without symptoms of disease) were sacrificed at 250 days pi for Western blot and histopathological analysis of tissues.

References

1. Collinge, J., Sidle, K. C., Meads, J., Ironside, J. & Hill, A. F. Molecular analysis of prion strain variation and the aetiology of 'new variant' CJD. *Nature* 383, 685-690 (1996).
2. Bruce, M. E. et al Transmissions to mice indicate that 'new variant' CJD is caused by the BSE agent. *Nature* 389, 498-501 (1997).
3. Hill, A. F. et al The same prion strain causes vCJD and BSE. *Nature* 389, 448-450 (1997).
4. Will, R. G. et al A new variant of Creutzfeldt-Jakob disease in the UK. *Lancet* 347, 921-925 (1996).
5. Prusiner, S. B. Prions. *Proc. Natl. Acad. Sci. USA* 95, 13363-13383 (1998).
6. Enari, M., Flechsig, E. & Weissmann, C. Scrapie prion protein accumulation by scrapie-infected neuroblastoma cells abrogated by exposure to a prion protein antibody. *Proc. Natl. Acad. Sci. USA* 98, 9295-9299 (2001).
7. Peretz, D. et al. Antibodies inhibit prion propagation and clear cell cultures of prion infectivity. *Nature* 412, 739-743 (2001).
8. Jackson, G. S. et al. Reversible conversion of monomeric human prion protein between native and fibrilogenic conformations. *Science* 283, 1935-1937 (1999).
9. Jackson, G. S. et al. Multiple folding pathways for heterologously expressed human prion protein. *Biochim. Biophys. Acta* 1431, 1-13 (1999).
10. Bueler, H. et al. Normal development and behaviour of mice lacking the neuronal cell-surface PrP protein. *Nature* 356, 577-582 (1992).
11. Beringue, V. et al. Regional heterogeneity of cellular prion protein isoforms in the brain. *Brain*.
12. Beringue, V. et al. Opposite effects of dextran sulfate 500, the polyene antibiotic MS-8209, and Congo red on accumulation of the protease-resistant isoform of PrP in the spleens of mice inoculated intraperitoneally with the scrapie agent. *J. Virol.* 74, 5432-5440 (2000).
13. Souan, L. et al. Modulation of proteinase-K resistant prion protein by prion peptide immunisation. *Eur. J Immunol.* 31, 2338-2346 (2001).
14. Heppner, F. L. et al. Prevention of scrapie pathogenesis by transgenic expression of anti-prion protein antibodies. *Science* 294, 178-182 (2001).
15. Westaway, D & Carlson, G. A. Mammalian prion proteins: enigma, variation and vaccination. *TIBS* 27, 301-307 (2002).
16. Klein, M. A. et al. PrP expression in B lymphocytes is not required for prion neuroinvasion. *Nat. Med.* 4, 429-433 (1998).
17. Montrasio, F. et al. Impaired prion replication in spleens of mice lacking functional follicular dendritic cells. *Science* 288, 1257-1259 (2000).
18. Brown, K. L. et al. Scrapie replication in lymphoid tissues depends on prion protein-expressing follicular dendritic cells. *Nat. Med.* 5, 1308-1312 (1999).
19. McKenzie, D., Kaczkowski, J., Marsh, R. & Aiken, J. Amphotericin B delays both scrapie agent replication and PrP-res accumulation early in infection. *J. Virol* 68, 7534-7536 (1994).
20. Ingrosso, L., Ladogana, A. & Pocchiari, M.Congo red prolongs the incubation period in scrapie-infected hamsters. *J. Virol.* 69, 506-508 (1995).
21. Farquhar, C., Dickinson, A. & Bruce, M. Prophylactic potential of pentosan polysulphate in transmissible spongiform encephalopathies. *Lancet* 353, 117 (1999).
22. Brown, P. Drug therapy in human and experimental transmissible spongiform encephalopathy. *Neurology* 58, 1720-1725 (2002).
23. Sethi, S., Lipford, G., Wagner, H. & Kretzschmar, H. Postexposure prophylaxis against prion disease with a stimulator of innate immunity. *Lancet* 360, 229-230 (2002).
24. Sigurdsson, E. M. et al. Immunisation delays the onset of prion disease in nice. *Am. J. Pathol.* 161, 13-17 (2002).
25. Bard, F. et al. Peripherally administered antibodies against amyloid β-peptide enter the central nervous system and reduce pathology in a mouse model of Alzheimer disease. *Nat. Med.* 6, 916-919 (2000).
26. Brandner, S. et al. Normal host prion protein necessary for scrapie-induced neurotoxicity. *Nature* 379, 339-343 (1996).
27. Anstee, D. J. et al. New monoclonal antibodies in CD44 and CD58: their use to quantify CD44 and CD58 on normal human erythrocytes and to compare the distribution of CD44 and CD58 in human tissues. *Immunology* 74, 197-205 (1991).
28. Avent, N. D. et al. Protein-sequence studies on Rh-related polypeptides suggest the presence of at least two groups of proteins which associate in the human red-cell membrane. *Biochem. J.* 256, 1043-1046 (1988).
29. Dickinson, A. G., Meikle, V. M. & Fraser, H. Identification of a gene which controls the incubation period of some strains of scrapie agent in mice. *J. Comp. Pathol.* 78, 293-299 (1968).
30. Wadsworth, J. D. et al. Tissue distribution of protease resistant prion protein in variant Creutzfeldt-Jakob disease using a highly sensitive immunoblotting assay. *Lancet* 358, 171-180 (2001).

All publications mentioned in the above specification are herein incorporated by reference. Various modifications and variations of the described antibodies, methods and uses of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. An isolated PrP binding antibody or antigen or antigen binding fragment thereof comprising a heavy chain variable domain sequence encoded by the nucleic acid sequence of SEQ ID NO: 1 and a light chain variable domain sequence encoded by the nucleic acid sequence of SEQ ID NO: 2.

2. An isolated PrP binding antibody or antigen or antigen binding fragment thereof comprising a heavy chain variable domain sequence encoded by the nucleic acid sequence of SEQ ID NO:3 and a light chain variable domain sequence encoded by the nucleic acid sequence of SEQ ID NO:4.

3. An isolated PrP binding antibody or antigen that contains the same $V_H$ CDRs 1, 2 and 3 as encoded by the nucleotide sequence of SEQ ID NO:1 and $V_L$ CDRs 1, 2, and 3 as encoded by the sequence of SEQ ID NO:2 or an antigen binding fragment of said antibody.

4. An isolated PrP binding antibody that contains the same $V_H$ CDRs 1, 2 and 3 as encoded by the nucleotide sequence of SEQ ID NO: 3 and $V_L$ CDRs 1, 2, and 3 as encoded by the sequence of SEQ ID NO: 4 or an antigen binding fragment of said antibody.

5. An isolated nucleic acid sequence selected from the group consisting of SEQ ID NO:1, SEQ ID NO:2, SEQ ID NO:3 and SEQ ID NO:4.

6. An isolated polypeptide encoded by nucleic acid selected from the group consisting of SEQ ID NO:1, SEQ ID NO:2, SEQ ID NO:3, and SEQ ID NO:4.

7. A composition comprising an antibody of claim 1.

8. A composition comprising an antibody of claim 2.

9. A composition comprising an antibody of claim 3.

10. A composition comprising an antibody of claim 4.

11. A composition comprising nucleic acid of claim 5.

12. A composition comprising a polypeptide of claim 6.

* * * * *

SEQUENCE LISTING

<160> NUMBER OF SEQ ID NOS: 4

<210> SEQ ID NO 1
<211> LENGTH: 414
<212> TYPE: DNA
<213> ORGANISM: Homo sapiens

<220> FEATURE:
<223> OTHER INFORMATION: ICSM35VH

<400> SEQUENCE: 1

| | | | | | |
|---|---|---|---|---|---|
| atggaatgga | cctgggtcat | tctcttcctc | ctgtcagtaa | ctgaaggtgt | ccactcccag | 60 |
| gttcagctgc | agcagtctgg | acctgagctg | gtgaagcctg | gggcctcagt | gaagatttcc | 120 |
| tgcaaggctt | ctggctacac | attcagtaac | tcctggatga | actgggtgaa | gcagaggcct | 180 |
| gggaaaggtc | ttgagtggat | tggacggatt | tatcctgaat | atggacatgc | tgactacaat | 240 |
| gggaagttcg | aaggcaaggc | cacactgact | gctgacagat | cctccagcac | agcctacatg | 300 |
| cacctcagca | gcctgacgtc | tgaggactct | gcggtctact | tctgtgcacg | agccccacta | 360 |
| cggtacccct | actttgacta | ctggggccaa | ggcaccactc | tcacagtctc | ctca | 414 |

<210> SEQ ID NO 2
<211> LENGTH: 381
<212> TYPE: DNA
<213> ORGANISM: Homo sapiens
<220> FEATURE:
<223> OTHER INFORMATION: ICSM35VK

<400> SEQUENCE: 2

| | | | | | |
|---|---|---|---|---|---|
| atggtgtcca | cagctcagtt | ccttggtctc | ctgttgctct | gttttcaagg | taccagatgt | 60 |
| gatatccaga | tgacacagac | ttcatcctcc | ctgtctgcct | ctctgggaga | cagagtctcc | 120 |
| atcagttgca | gggcaagtca | ggacatttcc | aattatttaa | actggtatca | gcagaaacca | 180 |
| gatggaactg | ttaaactcct | gatccactac | acatcaagat | tacactcaag | gagtcccatc | 240 |
| aaggttcagt | ggcagtgggt | ctggaacaga | ttattctctc | accattagcc | acctggagga | 300 |
| agaagatatt | gccacttact | ttgccaacag | ggtaatgcgc | ttcctccgac | gttcggtggc | 360 |
| ggcaccaagc | tggaaatcaa | a | | | | 381 |

<210> SEQ ID NO 3
<211> LENGTH: 405
<212> TYPE: DNA
<213> ORGANISM: Homo sapiens
<220> FEATURE:
<223> OTHER INFORMATION: ICSM18VH

<400> SEQUENCE: 3

| | | | | | |
|---|---|---|---|---|---|
| atggaatgga | gctgggtttt | cctcttcctc | ctgtcaggaa | ctgcaggtgt | cctctctgag | 60 |
| gtccagctac | aacagtctgg | acctgagctg | gtgaagcctg | gtcttcagt | gaagatatcc | 120 |
| tgcaaggcat | ctagaaacac | attcactgac | tataacttgg | actgggtgaa | gcagagccat | 180 |
| ggaaagacac | ttgagtggat | tggaaatgtt | tatcctaaca | atggtgttac | tggctacaac | 240 |
| cagaagttca | ggggtaaggc | cacactgact | gtagacaagt | cctccagcac | agcctacatg | 300 |
| gagctccaca | gcctgacatc | tgaggactct | gcagtctatt | actgtgccct | ttattactac | 360 |
| gatgtctctt | actggggcca | agggactctg | gtcactgtct | ctgca | | 405 |

<210> SEQ ID NO 4
<211> LENGTH: 711
<212> TYPE: DNA
<213> ORGANISM: Homo sapiens
<220> FEATURE:
<223> OTHER INFORMATION: ICSM181c

```
<400> SEQUENCE: 4
atggatttac aggtgcagat tatcagcttc ctgctaatca gtgcctcagt cataatatcc      60
agaggacaaa ttgttctcac ccagtctcca gcaatcatgt ctgcatctcc aggggagaag     120
gtcaccatga cctgcagtgc cagctcaagt gtaagttaca tgcactggta ccagcagaag     180
tcaggcacct cccccaaaag atggatttat gacacatcca aactggcttc tggagtccct     240
gctcgcttca gtggcagtgg gtctgggacc tcttactctc tcacaatcag cagtatggag     300
gctgaagatg ctgccactta tttctgccac cagtggagaa gtaacccata cacgttcgga     360 gggggggacca agctggaaat aaaacgggct gatgctgcac caactgtatc catcttccca     420
ccatccagtg agcagttaac atctggaggt gcctcagtcg tgtgcttctt gaacaacttc     480
taccccaaag acatcaatgt caagtggaag attgatggca gtgaacgaca aaatggcgtc     540
ctgaacagtt ggactgatca ggacagcaaa gacagcacct acagcatgag cagcaccctc     600
acgttgacca aggacgagta tgaacgacat aacagctata cctgtgaggc cactcacaag     660
acatcaactt cacccattgt caagagcttc aacaggggag agtgttagtg a              711
```